(12) United States Patent
Qiu et al.

(10) Patent No.: US 11,127,197 B2
(45) Date of Patent: Sep. 21, 2021

(54) INTERNAL LIGHTING FOR ENDOSCOPIC ORGAN VISUALIZATION

(71) Applicant: Siemens Healthcare GmbH, Erlangen (DE)

(72) Inventors: Feng Qiu, Pennington, NJ (US); Wei Hong, Skillman, NJ (US); Daphne Yu, Yardley, PA (US)

(73) Assignee: Siemens Healthcare GmbH, Erlangen (DE)

( * ) Notice: Subject to any disclaimer, the term of this patent is extended or adjusted under 35 U.S.C. 154(b) by 646 days.

(21) Appl. No.: 15/492,589

(22) Filed: Apr. 20, 2017

(65) Prior Publication Data
US 2018/0308278 A1 Oct. 25, 2018

(51) Int. Cl.
G06T 15/50 (2011.01)
G06T 15/08 (2011.01)
G06T 15/06 (2011.01)
G06T 15/80 (2011.01)
G06T 15/20 (2011.01)
G06T 15/00 (2011.01)
A61B 1/00 (2006.01)
G06T 15/04 (2011.01)

(52) U.S. Cl.
CPC ........ *G06T 15/506* (2013.01); *A61B 1/00009* (2013.01); *G06T 15/005* (2013.01); *G06T 15/06* (2013.01); *G06T 15/08* (2013.01); *G06T 15/205* (2013.01); *G06T 15/80* (2013.01); *G06T 15/04* (2013.01); *G06T 2210/41* (2013.01); *G06T 2215/12* (2013.01); *G06T 2215/16* (2013.01)

(58) Field of Classification Search
None
See application file for complete search history.

(56) References Cited

U.S. PATENT DOCUMENTS

| 2005/0119550 | A1* | 6/2005 | Serra ...................... G06T 19/00 600/407 |
| 2013/0229411 | A1 | 9/2013 | Choi |
| 2013/0328874 | A1 | 12/2013 | Smith-Casem et al. |
| 2014/0232719 | A1* | 8/2014 | Wahrenberg .......... G06T 15/506 345/424 |

(Continued)

FOREIGN PATENT DOCUMENTS

| EP | 3246881 A1 | 11/2017 |
| WO | WO0055812 A1 | 9/2000 |

(Continued)

OTHER PUBLICATIONS

Hedman, Peter, Tero Karras, and Jaakko Lehtinen. "Sequential monte carlo instant radiosity." IEEE Transactions on Visualization and Computer Graphics (2016).

(Continued)

*Primary Examiner* — Edward Martello

(57) ABSTRACT

Systems and methods are provided rendering a three-dimensional volume. Scan data representing an anatomical object of a patient is acquired. A boundary of the object is identified in the scan data. A first lightmap is positioned inside the boundary of the object. A second lightmap is positioned outside the boundary of the object. The three-dimensional volume of the object is rendered from the scan data with lighting based on the first lightmap and second lightmap.

20 Claims, 5 Drawing Sheets

(56) References Cited

U.S. PATENT DOCUMENTS

2014/0327690 A1 11/2014 McGuire et al.
2016/0206203 A1 7/2016 Yu et al.
2016/0292913 A1 10/2016 Wahrenberg

FOREIGN PATENT DOCUMENTS

WO WO2006099490 A1 9/2006
WO WO2012159671 A1 11/2012

OTHER PUBLICATIONS

Robb, Richard Arlin. "Virtual endoscopy: development and evaluation using the Visible Human datasets." Computerized Medical Imaging and Graphics 24.3 (2000): 133-151.
Extended European Search Report (EESR) dated Nov. 6, 2018 in corresponding European Patent Application No. 18167410.2.

* cited by examiner

INTERNAL LIGHTING FOR ENDOSCOPIC ORGAN VISUALIZATION

BACKGROUND

The present embodiments relate to medical imaging and visual lighting techniques.

Virtual endoscopy uses medical imaging, such as computed tomography (CT) or magnetic resonance (MR) scanning, combined with computer imaging to provide a non-invasive view of internal objects. Examples include scans of the abdominal area, the heart, the head, the lungs, rotational angiography of blood vessels in various body parts, and others. Based on the resulting volumetric data, the organs of interest are visualized and inspected from interior, e.g. "endo," viewpoints.

Using virtual endoscopy, a user may conduct virtual examinations of internal regions of a patient, simulating the way an actual endoscopy views the internal regions. Virtual endoscopy overcomes a traditional endoscopy's disadvantage that requires inserting a scope into a patient's body. As opposed to traditional endoscopy, virtual endoscopy may be a completely non-contact inspection method. Virtual endoscopy has many uses including teaching, diagnosis, intervention planning, and interoperative navigation among other uses. Due to the non-invasive nature, virtual endoscopy may be less risky and less expensive to a patient and/or hospital.

As a simulated procedure, virtual endoscopy functions best when the image is presented in a manner that is easy to view and analyze. The scan data collected by the medical imaging devices may provide structure and some texture, but lacks lighting. Artificial lighting may be added using computer rendering techniques. Prior implementations for virtual endoscopic rendering have used a synthetic point light at the camera or a directional light as a light source. The use of a single point light source generates shadows and dark regions in the image that prevent a proper analysis. Using multiple point sources may dramatically increase the computational requirement, preventing a system from providing real time imaging. Using an average or ambient illumination for the entire volume results in an unrealistic view.

SUMMARY

By way of introduction, the preferred embodiments described below include methods, computer readable media and systems for generating photorealistic views of an internal object using lightmaps. Multiple lightmaps may be placed and used together with optional synthetic lighting and path tracing-based rendering in order to enable photorealistic, in-context internal views. A first lightmap is positioned inside the object to illuminate the internal object and inner object boundary. A second lightmap is positioned outside an object with a certain distance from an outer object boundary to provide the main illumination on external objects. A translucent window on a region of the object may provide a depiction of both the inside of the object and any external objects as context. A photorealistic view of the internal object and external object may be rendered using path tracing and the first and second lightmaps.

In a first aspect, a method is provided for rendering a three-dimensional volume. Scan data representing an anatomical object of a patient is acquired. A boundary of the object is identified in the scan data. A first lightmap is positioned inside the boundary of the object. A second lightmap is positioned outside the boundary of the object. The three-dimensional volume of the object is rendered from the scan data with lighting based on the first lightmap and second lightmap.

In a second aspect, a method is provided for generating a photorealistic image of an organ. Scan data of the organ is acquired. The scan data is rendered to an image with illumination based on a first lightmap positioned inside the organ and a second lightmap positioned outside the organ.

In a third aspect, a system is provided for rendering a three-dimensional volume. The system includes a memory, a graphics processing unit, and a processor. The memory is configured for storing data representing an object in three dimensions. The graphics processing unit is configured to render illumination from a first lightmap positioned inside an object and a second lightmap positioned outside the object. The processor is configured to render an image of the object including the illumination.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION

Figure 1:
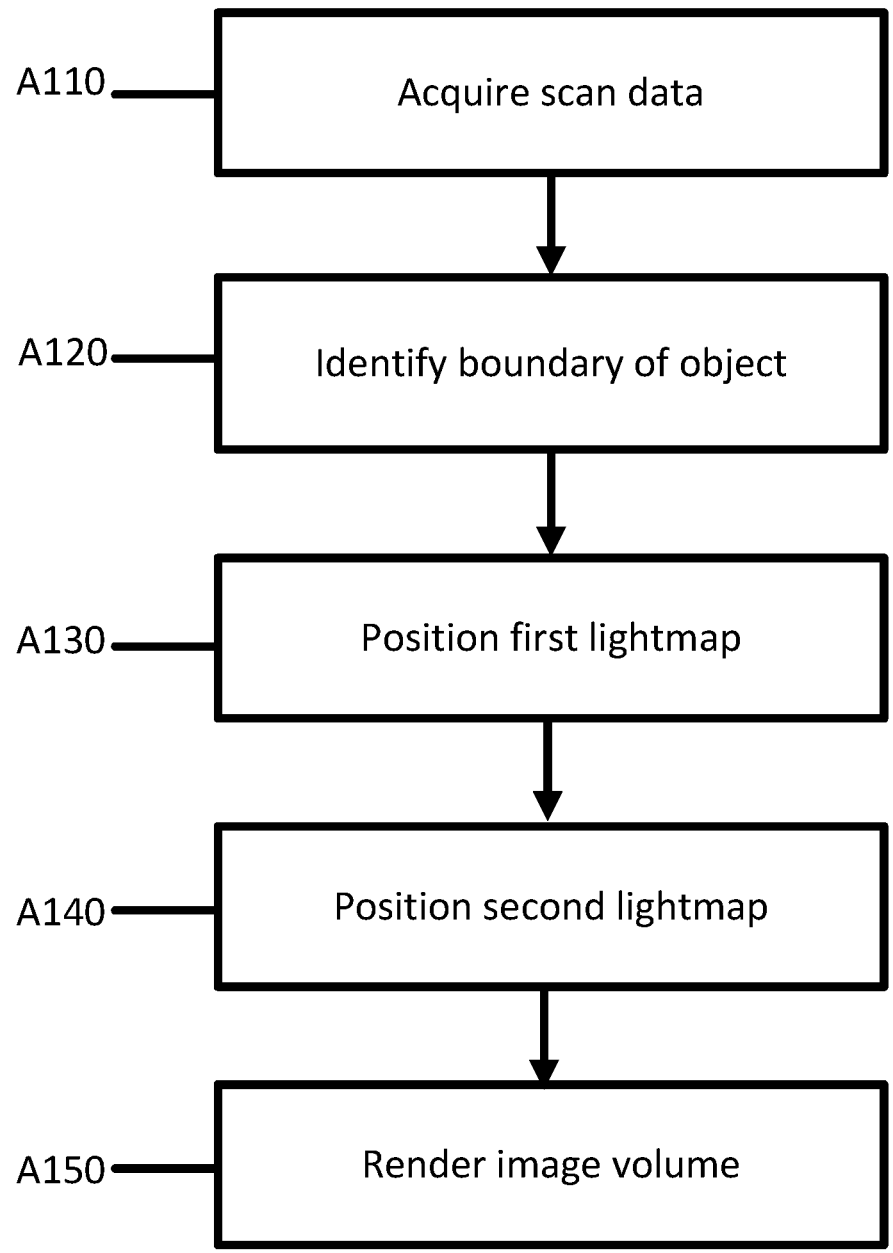
FIG. 1 is a flow chart of one embodiment of a method for providing photorealistic views of an internal object in a medical system.

Two lightmaps are used for path tracing-based volume rendering in virtual endoscopy. A boundary of an object of a patient is identified in scan data. A first lightmap is positioned inside the object. A second lightmap is positioned outside the object. The first lightmap provides illumination values for the interior of the object. The second lightmap provides illumination values for organs outside the object. A three-dimensional volume is rendered using a path tracing renderer with illumination rendered as a function of the first and second lightmaps.

Providing medical imaging with realistic lighting may be challenging. Medical volumes, from CT or MRI medical scan data, may be generated to provide a non-invasive view of an internal organ. Virtual endoscopy or computed endoscopy for example, are methods of imaging to assist diagnosis. The virtual endoscopy uses computer processing of the medical volume to provide simulated visualizations of patient specific organs similar or equivalent to those produced by standard endoscopic procedures.

For generating a medical image, surface and volume rendering use a variety of shading techniques and/or application of generic texture mappings related to specific surfaces. In order to visualize the volumes, a synthetic light source may be used to illuminate an internal object. A synthetic point light at a position of a camera viewpoint, or a directional light as a light source may be used to approximate the internal lighting of an actual endoscopy. Rendered lighting may involve two different types of illumination, direct and global illumination. Direct illumination may be the result of the light that hits a surface directly from a light source. Global illumination models how light is bounced off of the surface onto other surfaces. Multiple techniques may be used for rendering both direct and global illumination.

Ray tracing and path tracing are two different techniques for rendering the medical volume to a two-dimensional display image. Ray tracing may generate an image by tracing the path of light or vision through pixels in an image. Ray tracing tracks the encounters of the ray of light with the voxels of the medical volume. For example, the ray of light may collide with a virtual object at an angle. The ray of light may then reflect off into another virtual object. Each reflection or absorption may provide an illumination value that is captured and used by the ray tracing to generate the image.

In an example, light rays are traced from a virtual camera into a volume. Where the light rays intersect with objects, the rays are scattered and generate multiple rays to each light in the volume. Pixel values for lighting are calculated based on the material properties of the object with the amount of light that pixel is receiving from all the lights in the volume. Ray tracing is limited in that ray tracing only calculates direct lighting. For environmental or global lighting, ray tracing may sum all the direct lighting in the volume and apply the value across all the pixels in the volume (in addition to direct lighting). The result may appear unrealistic as the environmental lighting is uniformly distributed.

As opposed to ray tracing, path tracing computes global illumination based on actual light bounces. Path tracing is similar to ray tracing in that rays are cast from a virtual camera and traced through a simulated scene. Path tracing uses random sampling to incrementally compute a final image. Light photons with absorption and scattering based on the medical volume are modeled. Due to the random sampling, many photons along each viewing direction are modeled, each with random scattering and absorption forming a path through any number of scatter events. The random sampling process, e.g. a Monte Carlo algorithm for the path of each photon, allows for path tracing to render complex phenomena that are not computed in regular ray tracing.

In path tracing, rays are distributed randomly within each pixel in camera space, and, at each intersection with an object in the volume, a new reflection ray, pointing in a random direction, is generated. After a number of bounces, each ray exits the volume or is absorbed. When a ray (e.g., photon) has finished bouncing about in the volume, a value is calculated based on the objects the ray bounced against. The value is added to the average for the source pixel. Path tracing functions well for direct lighting, but may have issues rendering indirect lighting. Path tracing may use a radiosity method which divides a surface of an object into a large number of patches and computes how much each patch contributes to the illumination. Radiosity may be very inefficient, and unable to provide real time photorealistic images.

The samples in a path traced image are distributed over all pixels. The value of each pixel is the average of all the sample values computed for that pixel. The random components in path tracing cause the rendered image to appear noisy. The noise decreases over time as more samples are calculated. Generating a photorealistic image from path tracing may use a large computational requirement. The number of samples or bounces may be limited to increase efficiency, but may result in a less realistic image. Additionally, similarly to ray tracing, the environmental lighting in path tracing may result in a non-realistic image. With only a synthetic point source, the lighting may appear artificial to a user. For procedures and diagnosis that rely on a user's ability to detect and analyze the volume, non-realistic lighting may disadvantage the user.

Furthermore, use of point source lighting regardless of rendering technique may not provide context for a volume. Light from the point source may be blocked by walls of the internal object and/or may create shadows or dark areas in the volume. Simulated light rays from the point source may hit an object that blocks the rays, absorbs the rays, or reflects the rays. Areas outside the object or organ may not be illuminated, leaving a user without spatial contextual information.

With only a point light source, a virtual endoscopic image may be difficult to analyze. Multiple point light sources may be used, but the increase in computational requirements may prevent an image from being rendered in real time in response to user actions. A global illumination level may be increased across the entire image. The increase, however, may lead to unrealistic views of the object and exterior organs.

Methods and systems are provided that provide for realistic environmental lighting in medical imaging with path tracing for virtual endoscopy. Medical images are received. A boundary of an object is identified from the medical images. A first lightmap is positioned at a first distance inside the boundary. A second lightmap is positioned at a second distance outside the boundary. A medical volume is rendered by path tracing using the first lightmap and second lightmap. A translucent window may be rendered on the boundary.

The use of two lightmaps provides for an efficient realistic lighting that provides external context for a user. The use and positioning of the two lightmaps provide for environmental mapping and reflection mapping that may be used by a path-tracing renderer. The two lightmaps store a precomputed texture that may take full advantage of complex lighting textures that control the appearance of an object.

FIG. 1 depicts a diagram of one embodiment of a method for providing photorealistic images in a medical system. The method relates to the use and positioning of two lightmaps to provide lighting textures to an image rendered using a path tracing algorithm.

Figure 5:
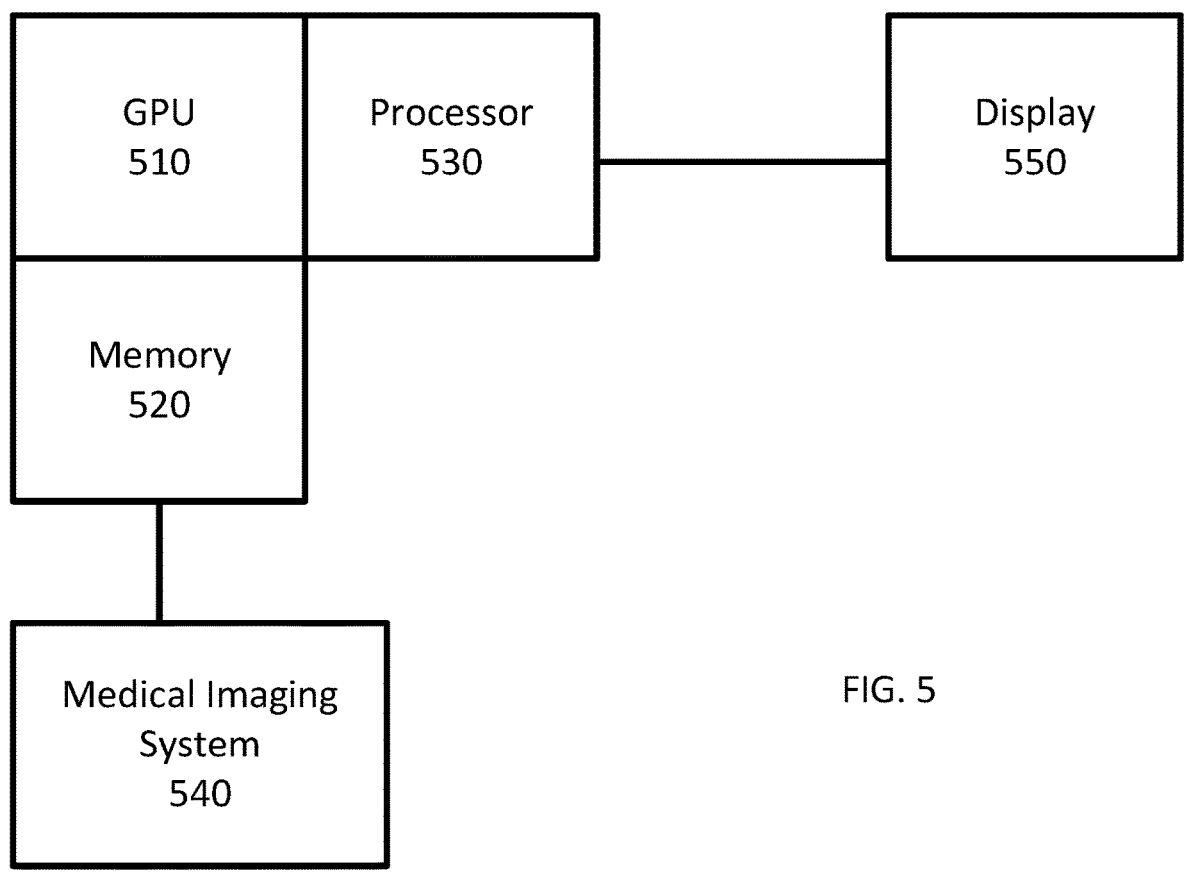
FIG. 5 is a block diagram of one embodiment of a medical system for providing photorealistic views of an internal object in a medical system.

The medical system of FIG. 5 or other medical system implements the acts. The system may be a medical imaging system, a hospital workstation, a medical server, or other secure medical data processing system. The medical system may or may not include a memory or database, such as patient medical record database and/or picture archiving and communications system (PACS).

The acts of FIG. 1 are performed in the order shown (numerical or top to bottom) or other orders. For example, acts A130 and A140 occur simultaneously or in any order. Additional, different, or fewer acts may be provided. Example additional acts include addition of a point source light or adjustment of a transparent section of the organ.

Images rendered using global illumination algorithms may appear more photorealistic than those using only direct illumination algorithms. However, such images are computationally more expensive and consequently much slower to generate. One common approach is to compute the global illumination of a scene and store that information with the geometry of the volume. The stored data may then be used to generate images from different viewpoints for generating walkthroughs of a volume without having to go through expensive lighting calculations repeatedly.

At act A110, the system acquires scan data representing anatomical objects of a patient. The scan data may be provided from a memory, a medical scanner, sensors, and/or other source. The data may be formatted as voxels. Each voxel may be represented by 3D location (e.g., x, y, z) and an intensity, scalar, or other information. In one embodiment, the scan data represents a patient. In the examples below, medical imaging or scanner data is used. In other embodiments, other types of data are used. A medical scanner may provide the data, such as a medical dataset representing a 3D region of the patient. Any type of medical data is obtained, such as computed tomography, magnetic resonance, positron emission tomography, single photon emission computed tomography, ultrasound, or another scan modality. Scan data representing a 3D volume is loaded as a medical dataset. The scan data may be from multiple two-dimensional scans or may be formatted from a 3D scan. The scan data may represent one or more objects, for example, the internal organs of a patient. The scan data may include an object such as a lumen, e.g. a hollow object that may be the focus of a virtual endoscopic procedure. Example lumens include vessels, organs of the digestive system, reproductive organs, the heart, ear canal, respiratory system, or other organs, tracts, or parts of the body with a lumen.

At act A120, the system identifies a boundary of an internal object of the patient in the scan data. The scan data may include one or more lumens or objects inside a patient. A lumen, for example, may represent a cavity or internal area of a tubular or hollow object. The objects may include other lumens, organs, or objects inside a patient. The boundary of the object may approximate the walls of the object. The boundary may be defined by a distance (or in the case of a hollow tube, a radius) from a centrally located point from the interior walls of the object. The central point may track or represent a location of a virtual camera placed inside the object. The central point may shift over time as the virtual camera travels through the object or may be in one position without shifting.

The boundary may be used to position the two lightmaps. An internal lightmap outside the boundary may be prevented from providing internal illumination or reflectance. An external lightmap inside the boundary, similarly would not be able to provide illumination or reflection for external objects.

The boundary may be identified using a segmentation algorithm. Thresholding, random walker, or other segmentation approaches may be used.

The segmented scan data may include a wireframe model or shape model of the interior of the patient without textures. The segmentation algorithm may assign a label to each pixel or voxel in the scan data. Similar labeled pixels or voxels may indicate similar objects that may provide for an edge or object boundary to be identified in the scan data. The boundary may be defined by the walls of the object, e.g. defined by the interior wall and exterior wall. Alternatively, the boundary may be a single line that approximates the walls of the object. In a 2D segment of the volume, the boundary may appear circular or ellipsoidal. For the 3D volume, the boundary may be cylindrically, ovoidal, or spherically shaped. Non-regular shapes may be used. The boundary may be stored in a memory as a collection of pixels or coordinate values. A dilation algorithm and/or filtering may be applied to enlarge and smooth the segmentation results.

While an accurate boundary may be desirable, the boundary may not need to be accurate to a certain degree. Automatic segmentation or a manual segmentation may be used to identify the boundary. A rough approximation of the boundary, for example, within 1, 5, or 10 voxels may be used. An estimation of the center of a wall of the object may be used with an estimated thickness to generate an estimated boundary. Alternative edge detection methods may be used. For example, an iso-surface, e.g. a surface that represents points of a constant value within a volume of space may also be used instead of object segmentation.

Figure 2:
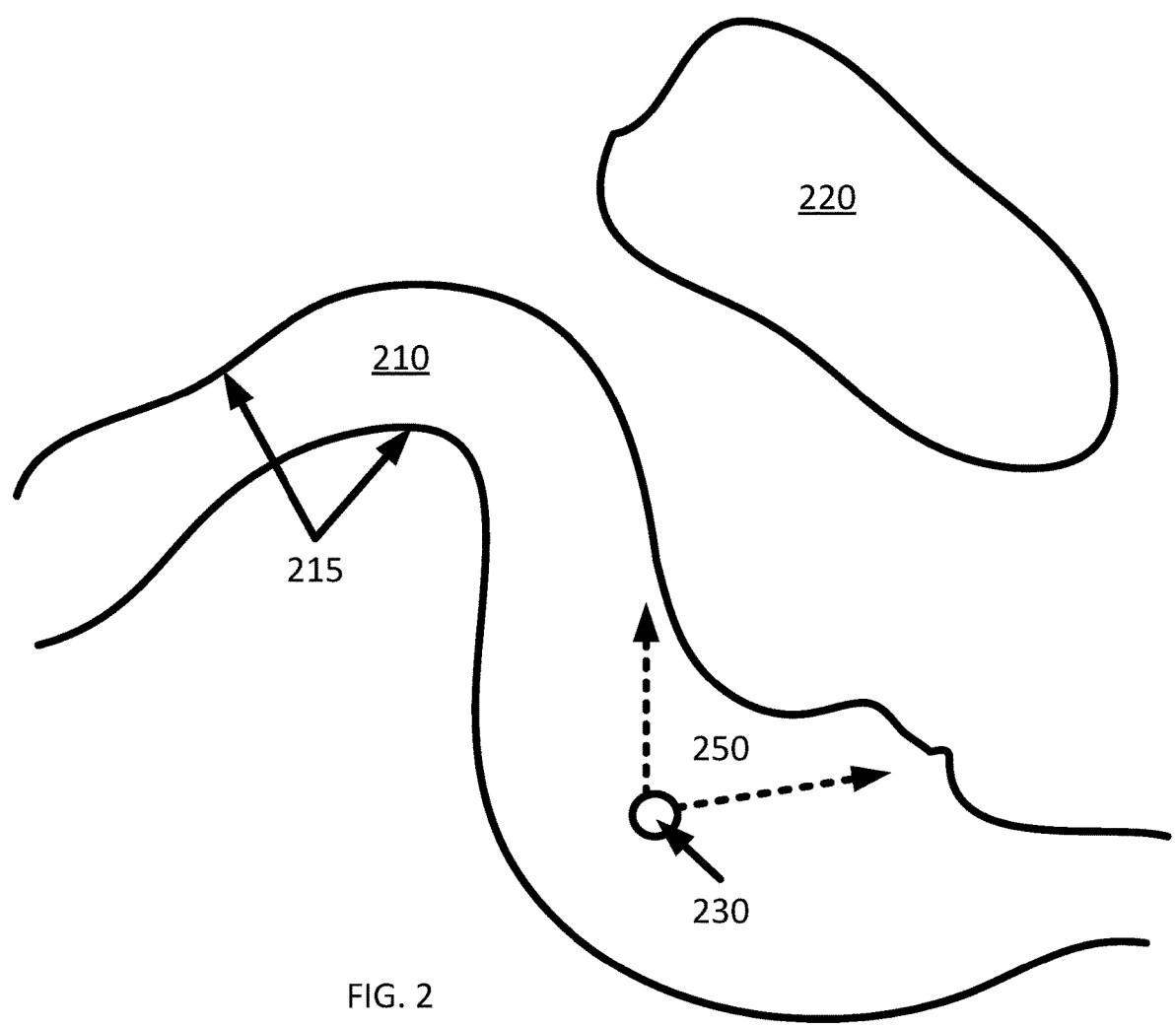
FIG. 2 illustrates a cross section view of an example internal object.

FIG. 2 depicts an example 2D cross section view of a 3D volume including an identified boundary 215. The figure includes an object 210 and an external object 220 outside the object 210. FIG. 2 further includes a virtual camera 230 placed at a camera position and a field of view 250 of the virtual camera 230. The field of view 240 includes a section of the object wall 215. The walls 215 of the object 210 have been depicted as a single line, however, in practice the object walls 215 may vary in width along the object 215. The walls 215 in FIG. 2 may be identified as the boundary in act A120.

At act A130, a first lightmap, or internal lightmap, is positioned inside the boundary 215. A lightmap may be a type of texture map that may be overlaid on an object to provide lighting detail or lighting values for rendering an image.

The positioning of the lightmaps is a function of distances relative to the object boundary 215. Improperly placed lightmaps within objects may introduce undesirable dark unlit areas and artifacts. The lightmap may be placed within the boundary 215 so that a selected center point of the lightmap is a minimum distance from the boundary 215. The selected position may be a position of a virtual camera. The object walls (and as such, boundary 215) may not be equidistant from the selected position. The first distance is the minimum distance possible so that, the entirely of the internal lightmap is inside the object and does not intersect with the boundary 215. In an example of a spherical lightmap, the entire sphere with a radius of the minimum distance fits within the object. In alternative embodiments, the lightmap intersects with the boundary 215.

Lightmaps may include elements that include lighting parameters referred to as lumels. The size of the lumels relates to the amount of detail in the map. Smaller lumels yield a higher resolution lightmap, providing finer lighting detail with a drawback of reduced performance and increased memory usage. For example, a lightmap scale of 2 lumels per unit may give a lower quality than a scale of 8 lumels per unit. The resolution of the lightmap may also be limited by the amount of disk storage space, bandwidth/download time, or texture memory available to the application.

The resolution of the lightmap may be dependent on the first distance. A larger lightmap, for example, may contain more lumels and as such, more information. For a spherical lightmap, a smaller radius leads to a smaller surface area for the lightmap, and less area to store and project lighting information. The surface area corresponds to the resolution that is the area, in pixels, available for storing one or more surface's lighting values. A spherical lightmap that has a selected point at the minimum distance from the boundary 215 may result in the largest possible amount of data stored in the lightmap without intersecting with the boundary 215.

The lightmaps may be generated in real time for each frame of the volume image. The lightmaps may be pre-computed. The lighting parameters stored in a lightmap may be derived from the type of tissue or object. The lighting parameters may be defined by a user or set at a default level. The lighting parameters may include resolution, irradiance, reflectance, intensity, translucency, absorbance, and others. An interior wall of a colon, for example, may have a range of reflectance values. A section of an object may have a predefined intensity. An interior wall of a stomach may include different values for irradiance or reflectance. Each material may have different values for different scenarios. The lighting parameters for the material may be globally used or may be patient specific. The lighting parameters may be derived from pervious endoscopic procedures and images captures with a physical camera and lighting system. The lighting parameters may be defined by a user.

The internal lightmap may be a reflectance lightmap. A reflectance lightmap includes reflectance values for the reflective properties of the surfaces in the volume. The reflective properties (amount, direction and colour) of surfaces may be modeled using a bidirectional reflectance distribution function (BRDF). BRDF is a function of four variables that defines how light is reflected at an opaque surface. The equivalent for transmitted light (light that goes through the object) is a bidirectional scattering distribution function (BSDF). The lightmaps may use either or both the BRDF or BSDF functions to control the lighting values of an object.

The lightmap may be a spherical, cubical, rectangular, cylindrical, shaped to confirm with the lumen, or other shaped map. Spherical mapping provides illumination as though the illumination was seen in the reflection of a reflective sphere through an orthographic camera. Cube mapped reflection is done by determining the vector that the object is viewed at. The camera ray is reflected about the surface of where the camera vector intersects the object. The reflected ray is then passed to the cube map to retrieve the lumel that provides the radiance value used in the lighting calculation. The rendered radiance value creates the effect that the object is reflective.

Figure 3:
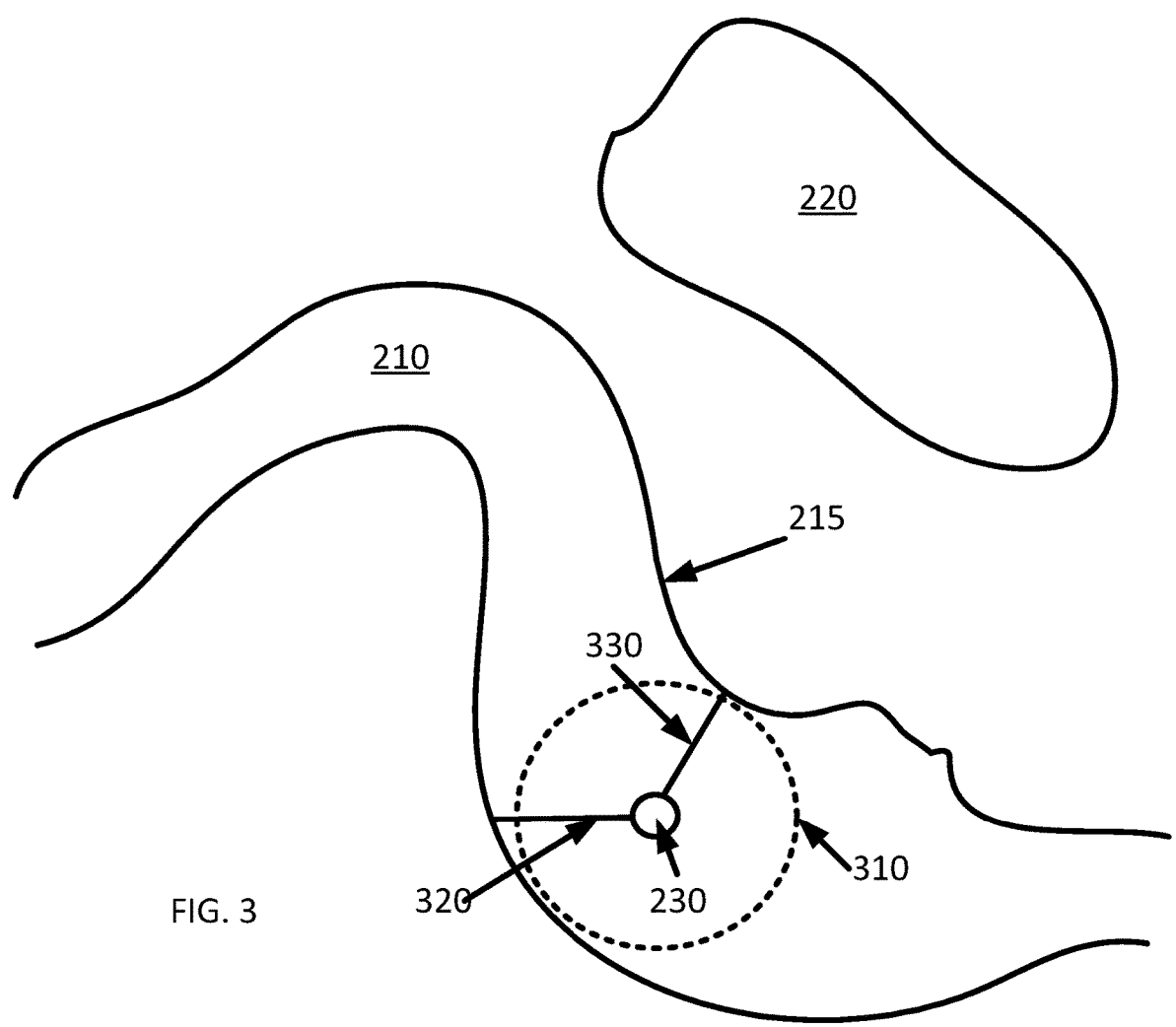
FIG. 3 illustrates a cross section view of the example internal object of FIG. 2 with an internal lightmap.

FIG. 3 depicts the positioning of the internal lightmap 310 inside the object 210. In FIG. 3, the internal lightmap 310 is positioned completely inside the focus object 210 illuminating the internal tissues. The internal lightmap 310 may be positioned centered at a position of the virtual camera 230, with the radius scaled with the minimum distance 330 from the virtual camera 230 to the object boundary 215. If the radius is scaled to exactly the minimum distance, a single point on the lightmap may touch the object boundary 215. As depicted in FIG. 3, the distance from the position of the virtual camera 230 to the object boundary 215 varies. For example, the distance 320 is larger than the distance 330. As the distance 330 is the minimum distance, that distance is chosen for positioning the lightmap. Alternatively, if the camera position was shifted to the left in FIG. 3, the distance 320 may be shorter and as such, the minimum distance.

The internal lightmap 310 may be positioned at a selected point inside the object other than the camera position. The internal lightmap 310 may be positioned so that the radius is smaller than the minimum distance from the selected position to the object boundary 215. The selected point may be, for example, a center point in the object. A center point may reside on a centerline that may be identified by calculating a perpendicular distance from each point on the boundary 215 and identifying the center.

FIG. 3 depicts a single image frame. For a procedure that requires multiple image frames, the camera and/or object may move or be altered. The movement of the camera or object may result in a change in the minimum distance from the position of the internal lightmap 310. The minimum distance may thus be adjusted for each frame. In order to maintain a high rendering framerate when the camera and/or object moves, an optimization technique to estimate the minimum distance may be used to precompute a distance volume of an acceptable resolution containing the minimum distance to the boundary 215 around the object. At each camera position, a lookup into the distance volume provides the minimum distance value at render time. The internal lightmap may be positioned not at a camera position, but at a center point or other selected point inside the object. A predefined, e.g. not interactive point, may provide for a high rendering framerate.

At act A140, a second lightmap, also referred to as an external lightmap, is positioned outside the boundary 215. The external lightmap may be an illuminance lightmap, a reflectance lightmap, or other type of lightmap. The external lightmap may be used to illuminate the surrounding organs beyond the focus object walls or provide lighting parameters of the exterior surfaces or tissues. The illumination outside the focus object walls may be used to support a translucent window or opaque organs in the rendered volume. The external lightmap may be positioned centered on a point at the camera location. The radius, in the case of spherical or cylindrical map, may be at least large enough to contain the focus object and not intersect with the boundary 215 in the viewing field. To achieve interactive computation of the maximum distance, a precomputed maximum distance volume may be used. Alternatively, for the maximum distance, a depth image of the object boundary 215 may be rendered with the current camera settings. The maximum depth value in the depth image is used to estimate the maximum distance of the object boundary 215 to the camera. The value may be specified or adjusted by the application.

The external lightmap may be pre-computed using rendering techniques such as ambient occlusion, phong shading, or photon mapping. Alternatively, the external lightmap may be generated in real time during a procedure.

The external lightmap may be adjusted to cover a larger volume to include or exclude other objects. For example, the size of the external lightmap may be adjusted to cover only an adjacent external object instead of the entirety of the patient. The external lightmap may be adjusted to cover a specific region or cavity of a patient.

Figure 4:
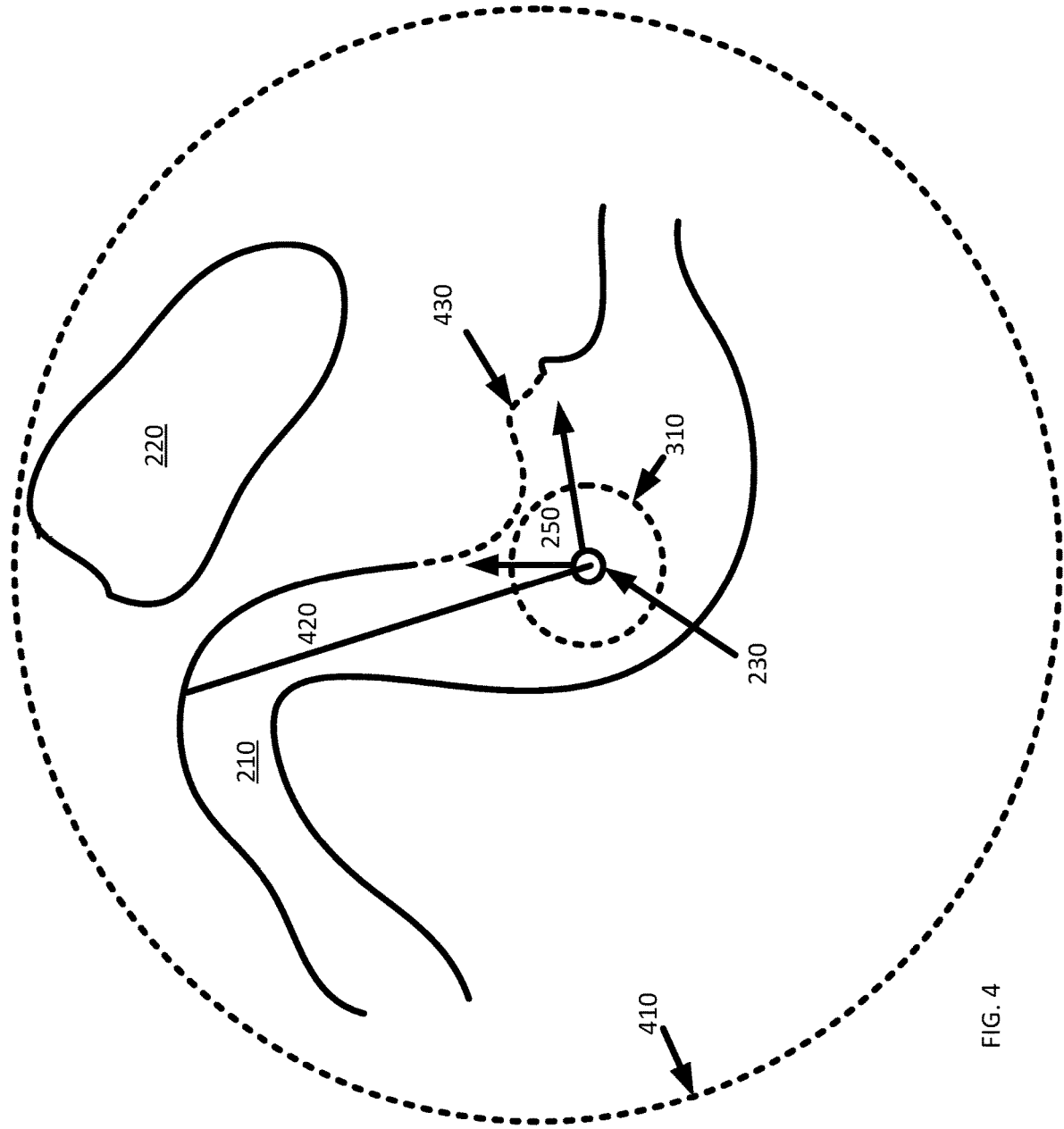
FIG. 4 illustrates a cross section view of the example internal object of FIG. 2 with an external lightmap.

FIG. 4 depicts a positioning of the external lightmap 410. The external lightmap 410 is positioned outside the focus object 210, illuminating the external organs 220. The external lightmap 410 may be positioned centered at the position of the virtual camera 230, with a radius scaled with at least the maximum distance from the camera to the object boundary 215. The maximum distance here may be represented by the distance 420. The external lightmap 410, as depicted in FIG. 4, is positioned to illuminate the entirely of the external object 220. FIG. 4 further depicts a translucent (or transparent) window 430 of the object walls so that a user may view the exterior of the object when the field of view 250 includes the translucent window 430. The entire boundary 215 may be partially translucent. FIG. 4 also depicts the internal lightmap 310 that may be used to provide lighting for the interior of the focus object 210.

In an embodiment, additional light sources may be used. One or more features may be detected in the scan data. A user may desire to see the feature with a separate light source. The light source may be placed at the feature point, above the feature point, or at a back of the feature point based on the use cases. Optionally, a light source such as point light or directional light may be used in combination with the lightmaps by using local shading techniques (for example, Phong shading) when the ray (for ray tracing) reaches a surface. The light source may be positioned at the camera location to simulate a traditional endoscopic procedure.

At act A150, an image is rendered from the scan data with lighting based on the internal lightmap 310 and external lightmap 410. The image may include a view from a virtual camera positioned inside the object. The image may include a view of externally objects outside the focus object, for example, by rendered a portion of the object transparent or not fully opaque. The scan data may provide a skeleton or wire mesh frame on which illumination textures are added by a rendering process based on the lightmaps 310, 410. The textures may include shading, color, and lighting components. The three-dimensional image may be rendered to be photo-realistic.

Path tracing may be used to render the scan data and textures. Using path tracing, light rays bounce around the volume, acquiring values that the path tracing algorithm uses to solve the rendering equation. A ray may collide with a surface of an object with a high reflectivity (energy of ray after hitting the surface), with some surface graininess (reflection/refraction) and so on. The attributes, such as the reflectivity of the tissues or objects may be defined by the lightmaps. As a ray continues to bounce around, each ray absorbs, reflects or splits into multiple new rays depending on the properties e.g. tissue that the ray interacts with. The new rays also bounce around, performing the same function. After a number of bounces the rays hit a light source, providing a final value, the initial amount of energy. The lighting effects is rendered based on an algorithm that solves an equation including the values.

A Monte Carlo algorithm may be used to solve the equation. A Monte Carlo algorithm for rendering lighting is a statistical method based on an estimation of how much light is redirected to a point by other objects in the volume by casting rays from the point in random directions above the surface and evaluating the values of the objects the rays intersect. The contribution of each one of the rays is then summed up and the resulting sum is divided by the total number of rays.

Volumetric path tracing-based rendering may be used to render the scan data. Volumetric path tracing provides path tracing with the effects of light scattering. As in the path tracing method, a ray is traced backwards from the eye on until the ray reaches the light source. In volumetric path tracing, scatter events may occur during the tracing. When a light ray hits a surface, an amount of the ray may get scattered into the media. Volumetric path tracing samples a distance from the transmittance along a ray. If the distance is less than the distance of the nearest surface intersection along the ray, a scatter occurred in the media and the path is evaluated from the scatter point rather than the point on the surface.

In virtual endoscopic, external organs may be visualized to provide contextual information. For example, in virtual colonoscopy, an image may be rendered with fisheye lens of 180-degree field of view (FOV), and a user may want to see through the colon wall that is within 45 degree FOV. Within the 45 degree FOV, the colon wall may be rendered as semi-transparent allowing the user to view the external organs outside the colon and in front of the camera. The portion of the wall that may be rendered semi-transparent may be referred to as a translucent window. The translucent window may benefit other views where location context is important. For example, for a view of the heart, a camera is positioned inside the heart to view the valves. Simultaneously and in the same image, the coronary surrounding the heart surface that is in front of the camera may be displayed.

The translucent window 430 may be expanded to cover an entirety of a colon wall. The level of transparency of the translucent window may be adjusted by a user. A user, for example, may set the object wall to be highly transparent to determine the context of the region in which the virtual camera is placed. After the user has determined the context, the user may shift the transparency to a lower level in order to visualize the object wall. The translucent window may be toggled on and off or adjusted by a user. The translucent window may be adjusted automatically to provide a view to the user.

The translucent window 430 and the view of the exterior organs or objects may be rendered in a photorealistic way by using the external lightmap 410. Without the external lightmap 410, the exterior would either not be illuminated or full of shadow effects or dark areas due to the blocking nature of an object's walls. The illumination provided by the interior lightmap may be separated from the external lightmap 410 to provide accurate lighting without confusing shadows. Alternatively, the illumination of a point source inside the object may be combined with the values from the exterior lightmap. In volumetric path tracing, at a sampling position on the rays, an algorithm checks if the ray is scattered according to the scattering probability value at the sampling position. When using a semi-translucent window or wall, if the sampling position is inside the semi-transparent window 430 of the image, the scattering probability may be modulated by a user controlled value. The higher the user controlled value, the more transparent is the translucent window.

The exterior of the object may be lighted by either illumination from the exterior lightmap, point light sources, or light rays from the interior of the object. The translucent (or transparent) window may provide scatter or absorption values for any rays that reflect or pass through the translucent window. Alternatively, the interior and exterior areas may be separately illuminated based on the two respective lightmaps. The internal lightmap may provide illumination for the interior. The external lightmap may provide illumination for the exterior. The lightmaps may be generated or adjusted individually or together to achieve a preferred lighting scheme.

The rendering of the scan data using the illumination and or reflectance values in the lightmaps results in a photorealistic image. A sequence of images may be provided as the image is built or rendered. Alternatively, for a given set of values of rendering parameters, a single image is output. The rendering parameters are a default set, set by the user, determined by a processor, or combinations thereof. The rendering parameters may include data consistency parameters. Data consistency parameters include windowing, scaling, level compression, data normalization, or others. The rendering parameters may include viewing design parameters. Viewing design parameters include type of camera, position of the camera, orientation of the camera, intrinsic parameters for viewing, or others. One or more use-case specific parameters may be provided. Use-case specific parameters are settings specific to a given use, such as a particular camera position for a given type of medical report or use of two cameras for stereoscopic viewing. Additional lighting parameters may be used to render the image. Lighting parameters may include additional light sources such as point light sources placed automatically or by a user. The additional light sources may include different types or levels of lighting. Different contrast or coloring may be used for different sources.

FIG. 5 shows a medical system for virtual endoscopy using internal and external lightmaps. The medical system includes a medical imaging system 540, a processor 530, a memory 520, a GPU 510, and a display 550. The processor 530, GPU 510, and the memory 520 are shown separate from the medical imaging system 540, such associated with being a computer or workstation apart from the medical imaging system 540. In other embodiments, the processor 530 and/or memory 520 are part of the medical imaging system 540. In alternative embodiments, the medical system is a workstation, computer, or server. For example, the medical imaging system 540 is not provided or is provided for acquiring data representing a volume, and a separate database, server, workstation, and/or computer is provided for identifying and positioning lightmaps and rendering a volume with illumination based on the lightmaps. Additional, different, or fewer components may be used.

The system is used for rendering a volume of a patient from scan data and two or more lightmaps. The system may be used to position lightmaps for one or more image frames in a virtual endoscopic procedure.

The computing components, devices, or machines of the medical system, such as the medical imaging system 520 and/or the processor 530 are configured by hardware, software, and/or firmware to perform calculations or other acts. The computing components operate independently or in conjunction with each other to perform any given act, such as the acts of any of the methods described above. The act is performed by one of the computer components, another of the computing components, or a combination of the computing components. Other components may be used or controlled by the computing components to scan or perform other functions.

The medical imaging system 540 is any now known or later developed modality for scanning a patient. The medical imaging system 540 scans the patient. For example, a C-arm x-ray system (e.g., DynaCT from Siemens), CT like system, or CT system is used. Other modalities include MR, x-ray, angiography, fluoroscopy, PET, SPECT, or ultrasound. The medical imaging system 540 is configured to acquire the medical imaging data representing the patient. The data is acquired by scanning the patient using transmission by the scanner and/or by receiving signals from the patient.

The memory 520 is a buffer, cache, RAM, removable media, hard drive, magnetic, optical, database, or other now known or later developed memory. The memory 520 is a single device or group of two or more devices. The memory 520 is within the system 540, part of a computer with the processor 530, or is outside or remote from other components.

The memory 520 is configured to store medical scan data, other data, lightmap data, lightmap positioning, camera and point source lighting positions, boundaries of internal objects in the medical scan data and/or other information. Rendered volumes with illumination are stored in the memory 520. The memory 520 may store a pre-computed position and size of each lightmap. The memory 520 may store pre-computed values for the lightmap.

The memory 520 is additionally or alternatively a non-transitory computer readable storage medium with processing instructions. The memory 520 stores data representing instructions executable by the programmed processor 530. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 530 is a general processor, digital signal processor, three-dimensional data processor, graphics processing unit, application specific integrated circuit, field programmable gate array, digital circuit, analog circuit, combinations thereof, or other now known or later developed device for processing data. The processor 530 is a single device, a plurality of devices, or a network. For more than one device, parallel or sequential division of processing may be used. Different devices making up the processor 530 may perform distinct functions, such as positioning a lightmap with as one device and rendering a volume with another device. In one embodiment, the processor 530 is a control processor and/or graphics processing unit of the medical imaging system 540. In another embodiment, the processor 530 is one or more graphics cards. The processor 530 operates pursuant to stored instructions to perform various acts described herein.

The processor 530 is configured to receive scan data of an object, identify a boundary 215 and position lightmaps. The boundary 215 may be identified in the scan data using segmentation. A first internal lightmap may be positioned inside the object. A second external lightmap may be positioned outside the object. The processor 530 or GPU 510 renders a volume with illumination based on the lightmaps. Additional light sources may be added to illuminated the object. The processor 530 or GPU 510 may render a portion of the object translucent or transparent to provide a view from the interior of the object to the exterior of the object.

The GPU 510 is a graphics chip, graphics card, multi-core processor or other device for parallel processing to perform volume rendering. The GPU 510 is part of a computer, workstation, server, or mobile device. The GPU 510 is configured by software, hardware, and/or firmware to implement volume rendering. Monte Carlo path tracing, volumetric path tracing, or other technique for probabilistically or stochastic simulation of scattering and/or absorption of photons is used to render illumination for the volume. The processor 530 and GPU 510 may operate in sequence or parallel for generating and positioning the lightmaps and rendering the image volume. The GPU 510 is configured by an application programming interface to render an image from the 3D scan data representing a patient. Using path tracing based rendering, a photorealistic image is rendered. Path tracing is a method developed to solve a rendering equation. Path tracing is a ray tracing technique, a technique where rays are traced throughout a scene, hit some surface in the scene and generates samples from the information of that surface.

The display 550 is a CRT, LCD, plasma, projector, printer, or other output device for showing an image. The display 550 displays the rendered volume. The display 550 may receive user input to adjust the display image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for rendering a three-dimensional volume, the method comprising:
   acquiring scan data representing an object inside of a patient;
   identifying in the scan data, a boundary of the object;
   providing a first lightmap inside the boundary of the object;
   providing a second lightmap outside the boundary of the object; and
   rendering the three-dimensional volume of the object from the scan data with lighting based on the first lightmap and second lightmap.

2. The method of claim 1, wherein rendering the three-dimensional volume comprises rendering with volumetric path tracing.

3. The method of claim 1, further comprising:
   rendering a portion of the boundary of the object transparent.

4. The method of claim 3, wherein the transparent portion provides a view of an external object from a camera position inside the object.

5. The method of claim 1, wherein the boundary is identified using segmentation of the scan data.

6. The method of claim 1, wherein the boundary is a wall of the object.

7. The method of claim 1, wherein the first lightmap is spherical and centered at a camera position inside the object, wherein the first lightmap has a radius smaller than a minimum distance from the camera position to the boundary.

8. The method of claim 1, wherein the second lightmap is spherical and centered at a camera position inside the object, wherein the second lightmap has a radius larger than a maximum distance from the camera position to the boundary.

9. The method of claim 1, wherein the first lightmap comprises a reflectance lightmap.

10. The method of claim 1, wherein the second lightmap comprises an illuminance lightmap.

11. The method of claim 1, further comprising:
    providing a synthetic light source;
    wherein lighting for the three-dimensional image is further rendered including the synthetic light source.

12. The method of claim 11, wherein the three-dimensional image is further rendered using local shading techniques.

13. A method for generating a photorealistic image of an organ, the method comprising:
    acquiring scan data of the organ; and
    rendering the scan data to an image with illumination based on a first lightmap positioned inside the organ and a second lightmap positioned outside the organ.

14. The method of claim 13, wherein the first lightmap is spherical and centered at a camera position inside the organ, wherein the first lightmap has a radius smaller than a minimum distance from the camera position to a wall of the organ and wherein the second lightmap is spherical and centered at the camera position inside the organ, wherein the second lightmap has a radius larger than a maximum distance from the camera position to the wall.

15. The method of claim 13, wherein rendering to the image is volumetric path tracing rendering.

16. The method of claim 13, further comprising:
    transparently rendering to the image with at least a portion of a wall of the organ.

17. A system for rendering a three-dimensional volume, the system comprising:
    a memory configured to store data representing an object in three dimensions;
    a graphics processing unit configured to render illumination from a first lightmap positioned inside the object and a second lightmap positioned outside the object; and
    a processor configured to render an image of the object including the illumination.

18. The system of claim 17, wherein the first lightmap is spherical and centered at a camera position inside the object, wherein the first lightmap has a radius smaller than a minimum distance from the camera position to a wall of the object and wherein the second lightmap is spherical and centered at the camera position inside the object, wherein the second lightmap has a radius larger than a maximum distance from the camera position to the wall.

19. The system of claim 17, wherein the graphics processing unit is further configured to render illumination based on a point light source.

20. The system of claim 17, wherein the graphics processing unit is configured to render illumination using volumetric path tracing.

* * * * *